United States Patent [19]

Gordon

[11] Patent Number: 5,328,578
[45] Date of Patent: Jul. 12, 1994

[54] CAPILLARY ELECTROPHORESIS WITH TRACKING SEPARATION FIELD

[75] Inventor: Gary B. Gordon, Saratoga, Calif.

[73] Assignee: Hewlett-Packard Company, Palo Alto, Calif.

[21] Appl. No.: 77,576

[22] Filed: Jun. 15, 1993

[51] Int. Cl.[5] .................. G01N 27/26; G01N 27/447
[52] U.S. Cl. ............................ 204/180.1; 204/299 R
[58] Field of Search ...................... 204/299 R, 180.1

[56] References Cited

U.S. PATENT DOCUMENTS 4,908,112  3/1990  Pace .................. 204/299 R

FOREIGN PATENT DOCUMENTS 376611  7/1990  European Pat. Off. .
1-49952  2/1989  Japan .................. 204/299 R Primary Examiner—John Niebling
Assistant Examiner—John S. Starsiak, Jr.

[57] ABSTRACT

A capillary electrophoresis system utilizes a square "ring" capillary. The capillary has a hair-pin bend at each corner of the square. An opening in each bend permits fluid and electrical coupling with a respective electrolyte-containing vial. A distributor selectively routes the opposite terminals of a power supply to opposing corners of the square so that a sample component of interest migrates continuously downstream. A detector determines when the sample component traverses a detection point along the capillary. This detection is used to determine a migration rate for the sample component. When the sample component is estimated to be midway between corners, the distributor switches from applying a voltage differential between a second upstream corner and the downstream corner to applying a voltage differential between the upstream corner and the second downstream corner. This permits the sample component to migrate downstream past the downstream corner. The sample repeatedly traverses the ring until a reading from the detector determines that satisfactory resolution has been achieved.

13 Claims, 7 Drawing Sheets

CAPILLARY ELECTROPHORESIS WITH TRACKING SEPARATION FIELD

BACKGROUND OF THE INVENTION

1. Field of the Invention

The present invention relates to chemical analytical systems and, more particularly, to such systems employing capillary electrophoresis to separate chemical sample components. A major objective of the present invention is to provide for convenient higher-resolution separations of sample components.

2. Description of the Related Art

Much of modern medical progress is due to advances in chemical analytical systems that permit an investigator to separate, identify and characterize various chemical moieties. A typical analytical procedure involves separating components of a sample mixture so that they can be individually identified and quantified, for example, using a form of spectroscopy.

Electrophoresis, like other classes of separation techniques such as chromatography, separates sample components by causing them to migrate at moiety-specific rates along a path. Electrophoresis applies an electric field to cause sample components to migrate at rates related to their charge-to-mobility ratios. As the different components separate, the molecules of each component diffuse so that single components form in bands. Each band can be characterized by a peak, where the component concentration is maximal, and a width, being the distance between points on either side of the peak where the concentration falls below some threshold criterion.

Roughly speaking, two sample components are resolved by a separation technique when their bands do not overlap. Accordingly, the resolving power of a separation technique is positively related with the peak separations it achieves and inversely related to the band spreading it incurs. To increase resolving power, peak separation must be increased proportionately relative to band width.

Due to diffusion, the resolution of a capillary electrophoresis system cannot be improved simply by increasing the length of the separation path. For example, if path length is doubled while the voltage differential across the path is held constant, then the electric field strength is halved. Migration velocities, which are proportional to field strength, are thus also halved. Transit times are quadrupled since distance is doubled and migration velocities are halved. Peak separations are doubled since, although time is quadrupled, the separating field is halved. Concomitantly, band widths, which expand proportionately with the square root of the transit time, are also doubled. Since peak separations and band widths are both doubled, there is no net gain in resolving power.

Increasing the voltage differential across the path can increase the resolving power of a capillary electrophoresis system. For a capillary of a given length, doubling the voltage differential doubles electric field strength. Doubling the electric field strength, in turn, doubles the migration rate and, thus, the differential migration rate. For a given length capillary, doubling the electric field causes separation to occur in half the time at twice the rate, so peak-to-peak separation is unchanged. Beneficially, however, diffusion is reduced by $2^{-\frac{1}{2}}$, resulting in a resolution increase of about 40%.

The extent to which resolution can be increased by increasing field strength is limited. The electric field causes the electrolytic medium through which the sample components migrate to heat. If the field is sufficiently strong, the resulting significant radial thermal gradients cause radial viscosity gradients. The viscosity of the electrolyte affects the migration rate of the sample components. The radial viscosity gradient thus results in a radial migration rate gradient, which in turn results in band broadening. Thus, reductions in band broadening due to diffusion can be partially or completely offset by band broadening due to radial migration rate gradients.

Accordingly, gains in resolution must be achieved by increasing voltage differentials without increasing field strengths beyond an optimal field strength range. This can be achieved by using longer capillaries. For example, for a given voltage differential, doubling the capillary length, halves the electric field strength. Diffusion is unchanged while band spreading due to migration rate differentials is reduced. Thus, a desired resolving power can be achieved by selecting a respective voltage differential and then selecting a capillary long enough so that electric field strength does not result in unacceptable migration rate gradients.

While the use of longer capillaries addresses the problem of excessive field strengths otherwise associated with greater voltage differentials, there are other more intractable problems with large voltage differentials. For example, voltage differentials of 30 kV are readily and economically achievable due to the prevalent use of 30 kV power supplies in the television industry. To achieve resolutions greater than those achievable using these readily available power supplies involves the use of much less economical alternatives. Moreover, the use of voltage differentials much above 30 kV incurs risks of arcing and corona.

Ancillary approaches to improving the resolution of a capillary electrophoresis system involve electro-osmotic flow control. Without such control, electro-osmotic flow is superimposed on the electrophoretic migration. The faster total flow decreases the time available for electrophoretic separation, thus decreasing the separation attainable for a given capillary length and separation voltage. Electro-osmotic flow can be reduced by column coating and applying sheath potentials. Each of these methods has its limitations: chemical specificity of coatings and pH-range limitations with sheath voltages.

Inevitably, no matter how great the resolving power of a capillary electrophoresis system, overlapping component bands will emerge. When overlapping bands occur, it would be desirable to resolve them further. However, in conventional electrophoresis systems, once sample components have traversed the separation path, there is no provision for further separation of the bands. Accordingly, what is needed is a system and method for achieving higher resolution systems without using excessive voltage differentials or field strengths. Preferably, such a system and method would permit increasing resolution through further processing.

SUMMARY OF THE INVENTION

The present invention moves a separating electric field to track sample components during the separation process. The extent of the electric field is less than the separation path length so that the voltage differential used to establish the field can be much less than would be required if the field were established by electrodes at respective ends of the path.

The present invention comprises a capillary means for defining a separation path, a power supply means for supplying a voltage differential, and a distributor means for distributing the voltage differential between pairs of electrode points along the separation path. Whereas, a conventional electrophoresis system has two electrode points at opposite ends of a capillary, the present invention requires at least three electrode points, at least one of which is intermediate.

A relatively low, manageable, and safe voltage between an intermediate electrode point and an upstream electrode point provides a relatively strong separation field. As a sample component approaches the intermediate electrode point, the distributor means switches so that a voltage differential is applied between an electrode point upstream of the intermediate electrode point and an electrode point downstream of the electrode point. This allows the sample component to migrate downstream past the intermediate electrode point. Subsequently, the distributor can switch again to supply a potential difference between the intermediate electrode point and a downstream electrode point so that the sample component continues its downstream migration away from the intermediate electrode point.

Preferably, migration rate determination means are provided for determining the migration rate of a sample component or group of sample components of interest. Typically, the migration rate determination means includes a detector, preferably operating in conjunction with a controller. The controller compares the time of a detection with a reference time, either a previous peak detection or the sample injection time, to determine the migration rate. The controller then uses this migration rate to set the distributor timing so that the sample or samples of interest are maintained within the separation field at all times during the separation process. Of course, the distributor timing can be determined from the detector output without explicitly determining a migration rate.

Closed and open separation paths are provided for. Like conventional electrophoretic systems, open embodiments include an initial electrode point and a terminal electrode point. In addition, open embodiments also include at least one intermediate electrode point. In a closed or "ring" embodiment, all electrode points are intermediate in that, for each electrode point, there is an upstream electrode point and a downstream electrode point.

Whereas a sample component passes each point along an open separation path only once, a sample component can pass each point along a closed separation path multiple times. A detector placed along a closed separation path can detect a sample component each cycle. Successive detections can be used to determine the migration rate of a sample component of interest so that distributor switching can be synchronized to keep the component of interest continuously within the separation field. Similar tracking using an open embodiment can be achieved using multiple detectors or by routing a capillary so that it winds through a detector multiple times.

The present invention provides both for separation fields of constant strength and separation fields of varying field strengths. Constant separation fields can be provided for closed embodiments with three or more electrode points and for open embodiments with four or more electrode points. A "constant-field" strategy achieves a constant separation field using a constant voltage differential: the voltage differential is applied between an upstream electrode point and a downstream electrode point so that a sample component sample can migrate downstream past an inactive intermediate electrode point.

An alternative "inch-worm" strategy applies a voltage differential between adjacent electrode points except when this puts a sample component at risk of reaching an activated electrode point. A "repulsive" voltage is applied to the electrode point immediately upstream of the sample component, while an "attractive" voltage is applied to the electrode point immediately downstream of the sample component. If the sample component reached the downstream electrode point while it was "attractive" the sample component could be dumped from the capillary. To avoid dumping, as the sample component approaches, the originally attractive electrode point is deactivated in favor of the next downstream electrode point. This permits the sample component to pass the inactivated electrode point. However, since the voltage differential is not between adjacent electrodes, field strength drops (unless the voltage differential is increased). As soon as the sample component is safely past the recently inactivated electrode, a repulsive voltage is applied to it. Thus, the sample component continues to migrate downstream from the newly repulsive electrode point under maximum field strength. The switching process iterates as the sample component approaches each successive downstream electrode point.

A key to the present invention is the ability to apply voltages to intermediate points along a separation path. This is accomplished by permitting fluid coupling between the interior of the separation capillary and a vial filled with electrolyte. A voltage applied to an electrode immersed in the external (to the capillary) electrolyte is conveyed through a hole in the capillary wall to the electrolyte in the vial. Preferably, the hole is formed in a downwardly extended U-shaped bend. Methods for fabricating holes with precisely suitable dimensions are disclosed herein. Sample components can migrate past the hole and the bend by applying a voltage between electrode points upstream and downstream of the hole and bend.

In a closed capillary system, there would be a problem if "spurious" sample components lapped or were lapped by "interesting" sample components. The spurious sample components could reach a detector about the same time as the interesting sample components, interfering with sample component identification and quantification. The present invention avoids this interference by purging leading and lagging sample components before they can lap or be lapped. The purging occurs as the sample components inevitably arrive at an electrode point activated with an attractive potential that draws the arriving components out of the capillary and into the vial.

A general advantage of the present invention is that it achieves high field strengths over long effective path lengths without requiring excessive voltage differentials. Closed configurations of the invention provide arbitrarily long effective path lengths with a relatively small fixed length capillary. This provides the further advantage that separation can proceed as long as necessary to effect a desired separation; in effect, the present invention provides a capability of "zooming in" on hard-to-separate peaks. As a corollary, separation can be stopped when the desired separation is achieved so that no time is wasted and analytical throughput is optimized. Sample position and separation progress can be monitored using a single detector in a closed configuration. The presents invention works for a wider range of components and over a wider pH range than do prior art electro-osmotic flow control alternatives. These and other features and advantages of the present invention are apparent from the description below with reference to the following drawings.

DETAILED DESCRIPTION

Figure 1:
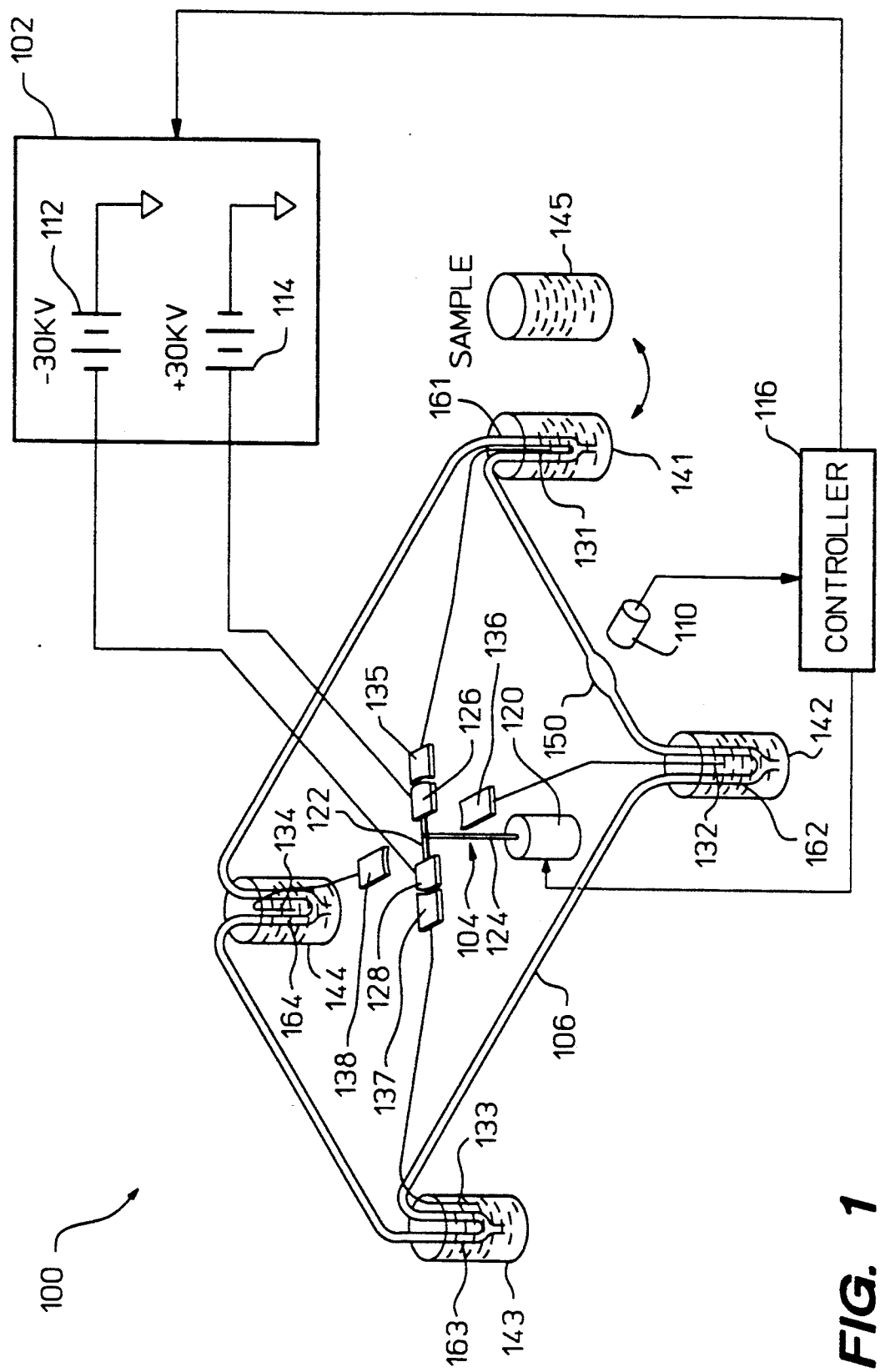
FIG. 1 is a schematic perspective illustration of a four-point closed capillary electrophoresis system in accordance with the present invention.

A preferred capillary electrophoresis system 100 is shown in FIG. 1. The principles of operation of system 100 are elaborated in conjunction with embodiments illustrated in FIGS. 2–4. A detailed description of the structure and operation of system 100 proceeds subsequently, with reference to FIGS. 5 and 6.

Figure 2:
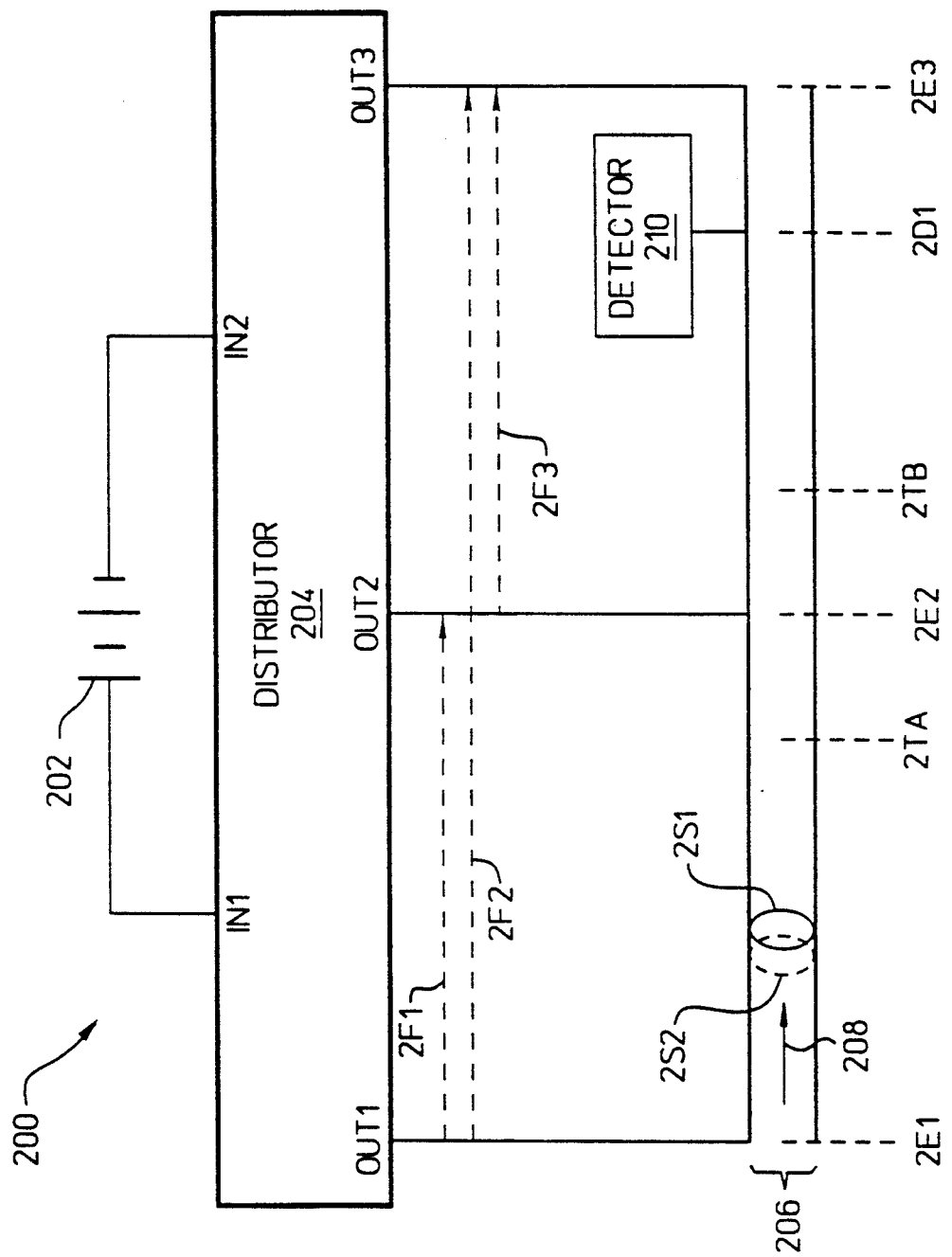
FIG. 2 is a schematic illustration of a three-point open capillary electrophoresis system in accordance with the present invention.

In accordance with the present invention, a capillary electrophoresis system 200 comprises a power supply 202, a distributor 204, and a capillary 206, as shown in FIG. 2. Capillary 206 defines a separation path, indicated by arrow 208, having a downstream direction indicated by the direction of arrow 208. Separation path 208 has three electrode points, an initial electrode point 2E1 at which a sample is injected, an intermediate electrode point 2E2, and a terminal electrode point 2E3. A detector 210 is located at a detection point 2D1 along separation path 208 and near terminal electrode point 2E3.

Distributor 204 is a 2×3 multiplexer. Its two inputs IN1 and IN2 are electrically coupled respectively to the positive and negative terminals of power supply 202. Its three outputs OUT1, OUT2 and OUT3 are respectively coupled to electrode points 2E1, 2E2 and 2E3.

In preparation for a cathodic separation, distributor 204 directs the positive voltage to initial electrode point 2E1 and a negative voltage to intermediate electrode point 2E2, establishing a separation field 2F1. Under this condition, a sample is injected into capillary 206 at initial electrode point 2E1. Separation field 2F1 draws the sample toward intermediate electrode point 2E2, with components progressing at rates dependent on their charge-to-mobility ratios. In this process, a sample component 2S1 begins to separate from another sample component 2S2.

In accordance with an inch-worm strategy, when sample component 2S1 reaches a transition point 2TA, distributor 204 switches from field 2F1 to 2F2 by redirecting the negative voltage to terminal electrode point 2E3. Separation field 2F2 has half the magnitude of separation field 2F1. Under the influence of separation field 2F2, sample component 2S1 migrates downstream past intermediate electrode point 2E2. Once sample component 2S1 reaches transition point 2TB, distributor 204 switches from field 2F2 to field 2F3. Under the influence of relatively strong separation field 2F3, sample component 2S1 continues downstream migration from electrode point 2E2 and toward terminal electrode point 2E3. Detector 210 then identifies and quantifies sample component 2S1 and other sample components as they migrate past detection point 2D1.

Figure 3:
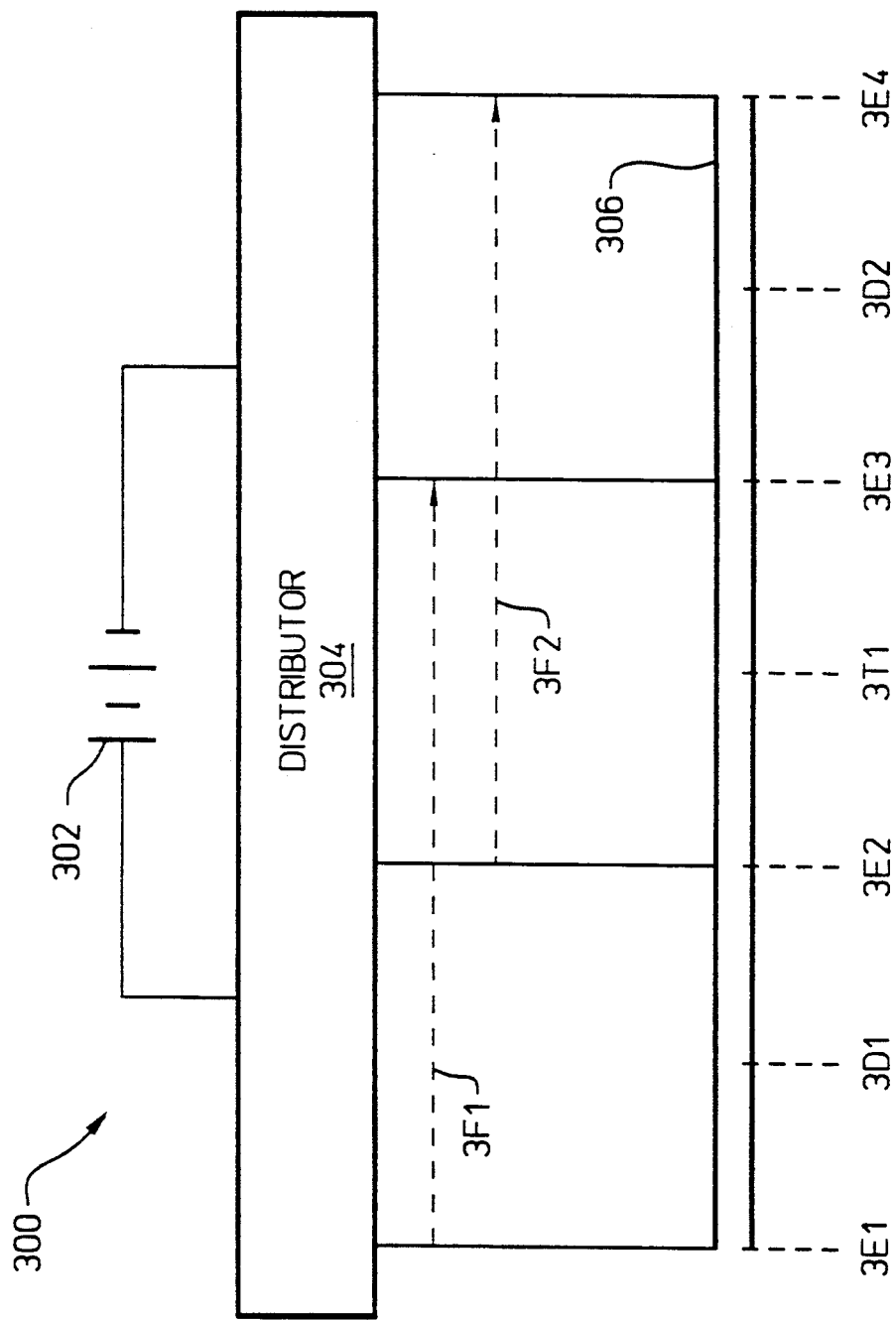
FIG. 3 is a schematic illustration of a four-point open capillary electrophoresis system in accordance with the present invention.

A four-point open electrophoresis system 300 in accordance with the present invention comprises a power supply 302, a distributor 304, and a capillary 306, as shown in FIG. 3. The positive and negative terminals of power supply 302 are coupled to respective inputs of distributor 304. Distributor 304 has four outputs respectively coupled to four electrode points of capillary 306. These four electrode points are an initial electrode point 3E1, an upstream intermediate electrode point 3E2, a downstream intermediate electrode point 3E3, and a terminal electrode point 3E4.

A sample is injected at initial electrode point 3E1 with distributor 304 directing voltages to electrode points 3E1 and 3E3 so that the sample migrates downstream as indicated by the corresponding field arrow 3F1. As the sample components migrate past detection point 3D1 they are detected by a detector (not shown). The time of a sample component detection is recorded. The recorded detection time is compared to the sample injection time to determine the migration rate of the sample component. This migration rate is used to estimate the time at which the sample component crosses subsequent points along the separation path defined by capillary 306.

The sample component migrates past 3E2. In accordance with a constant-field strategy, at the time the sample component is estimated to reach a first transition point 3T1, distribution 304 switches from field 3F1 to field 3F2 between electrode points 3E2 and 3E4. Under the influence of field 3F2, the sample component migrates downstream past electrode point 3E3. Component peaks are analyzed as they reach a second detector (not shown) at second detection point 3D2.

An advantage of the constant-field strategy used with electrophoresis system 300 is that a sample component is under the influence of a constant-strength separation field. By proper selection of field strength, this permits an entire separation to be conducted at an optimal field strength. In addition, relatively relaxed tolerances apply to the transition times since they do not affect the total duration a sample component is subjected to an optimal field.

Figure 4:
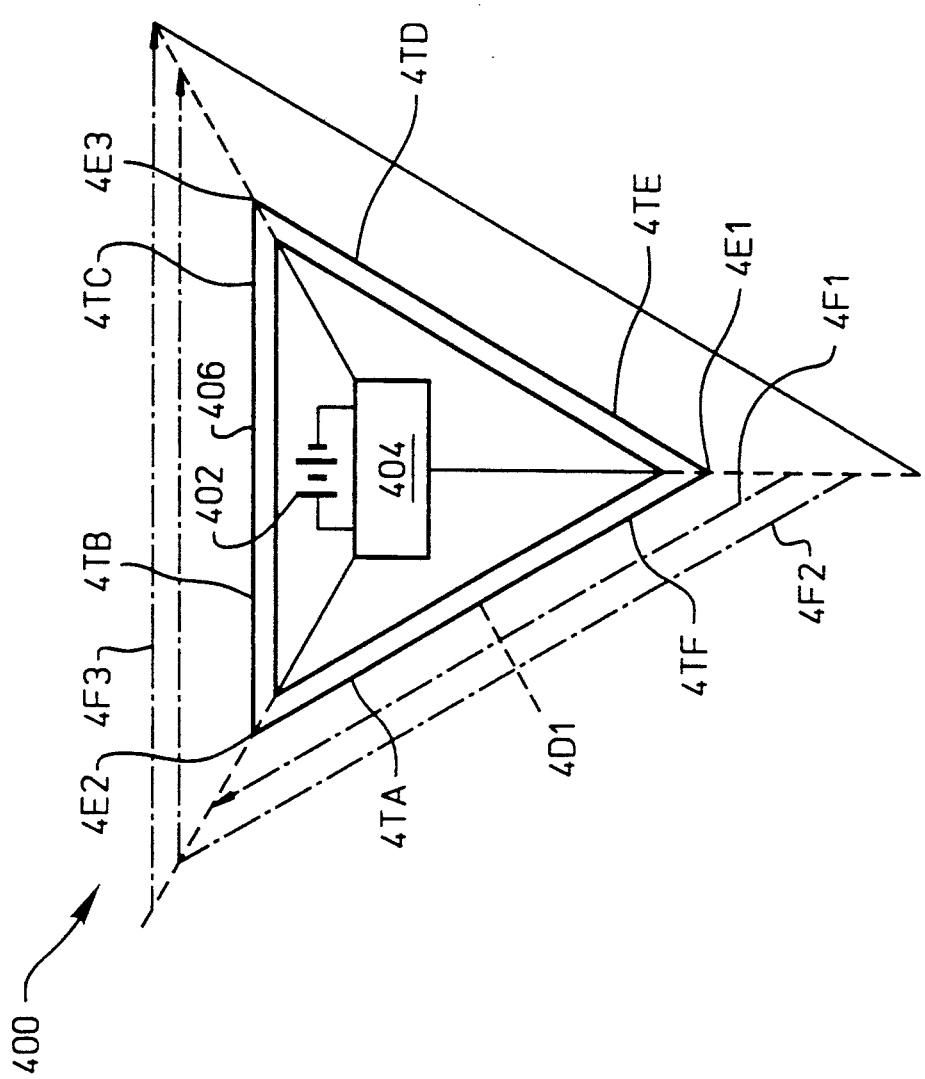
FIG. 4 is a schematic illustration of a three-point closed capillary electrophoresis system in accordance with the present invention.

A three-point closed capillary electrophoresis system 400 comprises a power supply 402, a distributor 404, and a triangularly configured capillary 406, as shown in FIG. 4. The positive and negative terminals of power supply 402 are coupled to the inputs of distributor 404, the three outputs of which are coupled respectively to electrode points 4E1, 4E2, and 4E3 of capillary 406.

An "inch-worm" separation begins with distributor 404 imposing a "single-legged" electric field 4F1 between electrode points 4E1 and 4E2 as a sample is injected at electrode point 4E1. A detector (not shown) detects sample components as they pass a detection point 4D1. The detection of a sample component of interest is used to determine the migration rate of that sample component. This migration rate determination is then used to determine the timing for distributor 404.

At the time the sample component is calculated to arrive at a transition point 4TA, distributor 404 switches to a relatively weak "double-legged" electric field 4F2. Under the influence of field 4F2, the sample component of interest can migrate downstream (clockwise in FIG. 4) past electrode point 4E2. At the time the sample component is calculated to arrive at a second transition point 4TB, distributor 404 switches to full-strength "single-legged" electric field 4F3 so that the sample component migrates downstream from electrode point 4E2 and toward third electrode point 4E3.

At the time the sample component is calculated to arrive at a transition point 4TC, distributor 404 switches to a relatively weak two-legged field between electrode points 4E2 and 4E1 so that the sample component can migrate downstream past electrode point 4E3. At the time the sample component is calculated to arrive at a transition point 4TD, distributor 406 switches to a relatively strong one-legged field between electrode points 4E3 and 4E1 so that the sample component migrates downstream toward electrode point 4E1. A similar inch-worm transition occurs at transition points 4TE and 4TF to permit the sample component to migrate downstream past electrode point 4E1, thus completing a cycle around capillary 406.

Near the beginning of each cycle around capillary 406, a sample component can be detected at detection point 4D1. This permits the migration rate to be determined and distributor timing adjusted accordingly. Once separation is completed, the same detector can be used for the final component identification and quantification. A significant advantage of the closed or "ring" embodiments of the present invention is that a single detector can be used for component tracking and for quantification.

It should be noted that a constant-field separation can also be employed in conjunction with a three-point closed capillary electrophoresis system. As a sample component approaches an electrode point (e.g., 4E3), the field is switched from between the second upstream electrode point (e.g., 4E1) and the approached point (e.g., 4E3) to between the first upstream point (e.g., 4E2) and the first downstream point (e.g., 4E1). Transitions can be made when a sample component is estimated to be about midway between electrode points. This formula works for closed electrophoresis system with any number of electrode points. In a three-point closed electrophoresis system, the second upstream electrode point and the first downstream electrode point are the same.

Figure 5:
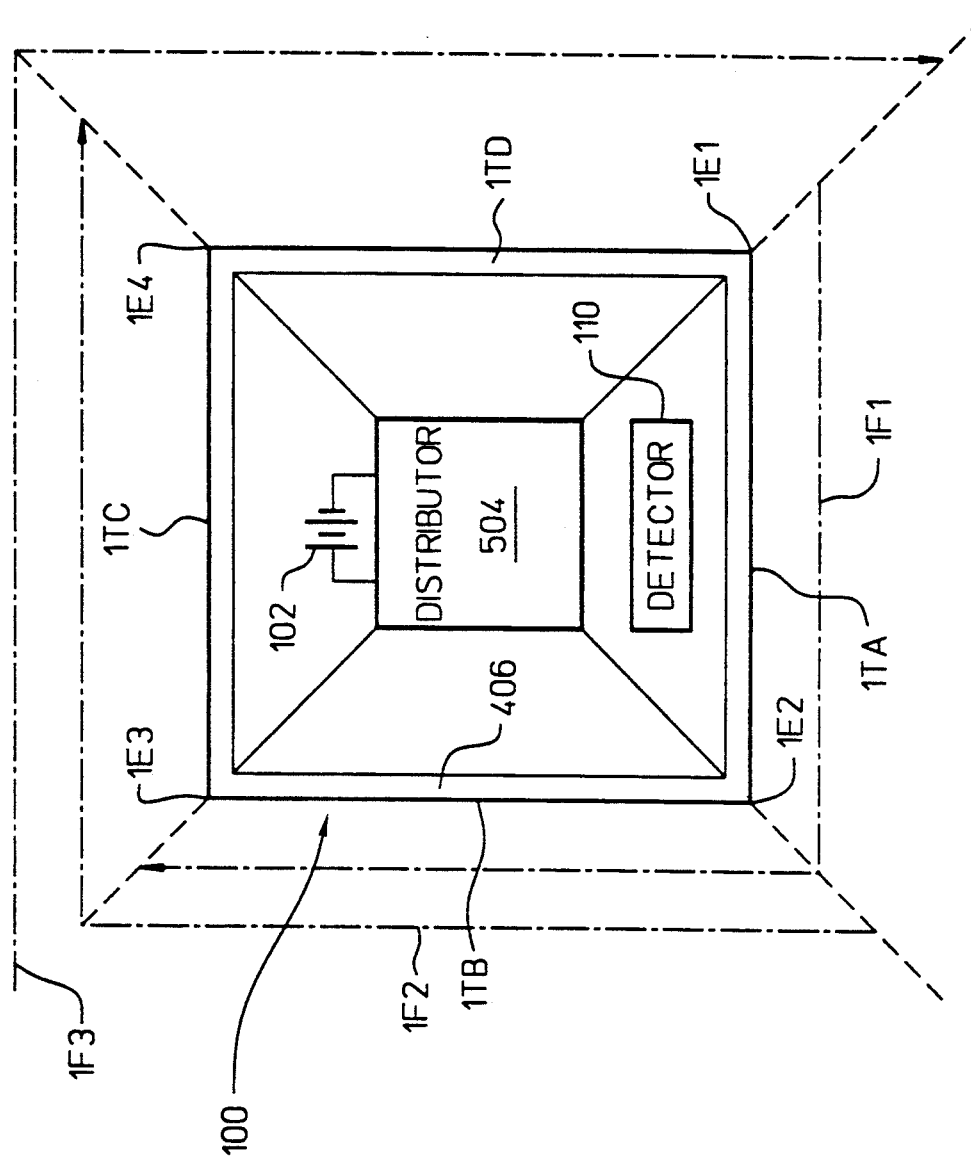
FIG. 5 is a schematic illustration of the four-point closed capillary electrophoresis system of FIG. 1.

Four-point closed electrophoresis system 100, shown in FIG. 1 and more schematically in FIG. 5, comprises a power supply 102, a power distribution system 504, a capillary 106, and a detector 110. The positive and negative terminals of power supply 102 are provided to the two inputs of distributor 104. The four outputs of distribution system 104 are respectively directed to electrode points 1E1, 1E2, 1E3, and 1E4 along capillary 106.

To implement a constant-field separation, power distribution system 504 applies a voltage differential between opposing electrode points 1E1 and 1E3, generating a two-legged separation field 1F1. Under the influence of field 1F1, a sample is injected into capillary 106 at electrode point 1E1; the sample components migrate downstream (clockwise in FIG. 1). Detector 110 detects sample components as they migrate past a first transition point 1TA, midway between electrode points 1E1 and 1E2. This detection is used to determine the migration rate of a sample component of interest. The migration rate is used to estimate the transitions times at which the sample component arrives at subsequent transition points. The estimated transition times govern the switching of distributor 504.

Under the influence of separation field 1F1, the sample component migrates downstream past electrode point 1E2. At the time the sample component is estimated to arrive at a second transition point 1TB midway between electrode points 1E2 and 1E3, distributor 104 switches to establish a voltage differential between opposing electrode points 1E2 and 1E4, generating a separation field 1F2. Under the influence of field 1F2, the sample component migrates downstream past electrode point 1E3. At the time the sample component is estimated to arrive at a third transition point 1TC midway between electrode points 1E3 and 1E4, distributor 104 switches to establish a voltage differential between opposing electrode points 1E3 and 1E1, generating a separation field 1F3. Under the influence of field 1F3, the sample component migrates downstream past electrode point 1E4.

In the next switching iteration, which begins as the sample component reaches a fourth transition point 1TD midway between electrode points 1E4 and 1E1, the sample component completes its first cycle of capillary 106. When the sample component reaches first transition point 1TA a second time, it is again detected by detector 110. This detection can be used to adjust the distributor timing. Further adjustments can occur in subsequent cycles, until the desired separation occurs. The last detection is used for component identification and quantification.

Four-point closed capillary electrophoresis system 100 is shown in greater detail in FIG. 1. Power supply 102 utilizes two 30 kV power supplies 112 and 114 arranged with opposing polarities to provide a 60 kV separation potential. This arrangement provides a minimum maximum differential with respect to earth ground, thereby minimizing a risk of arcing.

Detector 110 is an ultraviolet spectrometer capable of identifying and quantifying separated sample components. Detector 110 is optically coupled to capillary 106 for characterizing the spectral characteristic of the contents thereof; the output of detector 110 is coupled to a controller 116. Controller 116 matches predetermined patterns with the detector output to identify a sample component of interest and to adjust the timing of distributor 104 based on the migration rate of the sample component.

Distributor 104 comprises a distributor assembly 104, four electrodes 131–134 with associated leads, and four electrolyte-containing vials 141–144, as shown in FIG. 1. Distributor assembly 104 includes a motor 120, a rotor 122 including a shaft 124 and opposing brush contacts 126 and 128, and four switch contacts 135–138 which are coupled to respective electrodes 131–134. Serving as power distribution inputs, brush contacts 126 and 128 are continuously in electrical contact with respective positive and negative terminals of power supply 102. Serving as power distribution outputs, vials 141-144 are in fluid communication with electrolyte-filled capillary 106. Electrodes 131-134 are respectively immersed in vials 141-144. Electrodes 131-134 are selectively contacted by brush contacts 126 and 128 to apply respective 30 kV (repulsive for cathodic separation) and −30 kV (attractive) voltages to respective vials. Contact selection is determined by controller 116 and effected through its control of distributor motor 120. To reduce arcing, power supply 102 is switched off momentarily while distributor 104 is switched.

Figure 6:
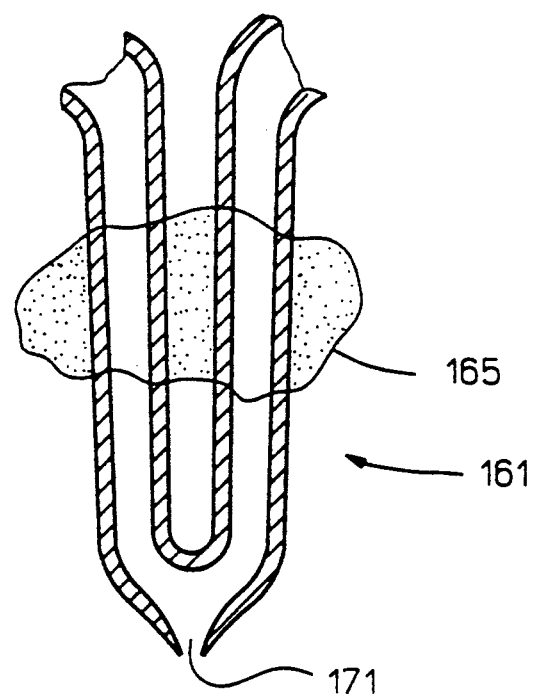
FIG. 6 is a sectional view of a joint of the electrophoresis system of FIG. 1.

Capillary 106 is formed from a single capillary tube, 120 centimeters (cm) long and 15 by 150 micron internal cross section. A bulb 150 is blown in the tube to form a detection volume at transition point 1TA along the separation path. The tube is bent into a square configuration; the ends of the tube are then joined at transition point 1TB to define a closed topology. The corners of the square are then bent into hair-pin U-formations, as indicated in FIG. 1, to define bends 16-164. Epoxy 165 is applied to provide rigidity to each bend, as indicated in FIG. 6. The outer radii of bend 161-164 are heated and respective holes 171-174 are blown therethrough. Holes 171-174 respectively define locations of electrode points 1E1-1E4.

Holes 171-174 provide for fluid communication between the separation path through the interior of capillary 106 and vials 141-144; since capillary 106 and vials 141-144 are all filled with electrolyte, capillary 106 is electrically coupled at electrode points 1E1-1E4 to respective vials 141-144. During electrophoresis, a sample component that reaches an activated electrode point will migrate out of capillary 106 and into the respective vial. However, a sample component can migrate past an opening if the respective electrode 131-134 is not activated.

During sample injection, vial 141 is replaced by a sample vial 145. In preparation for cathodic separation, rotor 122 is oriented so that a positive voltage is applied to electrode 131 and a negative voltage is applied to electrode 133; this is the condition illustrated in FIG. 1. In this case, 60 kV is distributed along 60 cm, resulting in a separation field of about 1000 V/cm. This condition causes a sample from sample vial 141 to be injected into capillary 106 through hole 171. Some of the sample is injected clockwise under the influence of separation field 1F1. However, a counterclockwise field, also extending between electrode points 1E1 and 1E3, injects sample upstream and counterclockwise into capillary 106. As described below, this spurious sample will be dumped subsequently during the separation process. Once a suitable volume of sample has been injected clockwise, power supply 102 is switched off and vial 145 is replaced with vial 141, filled with electrolyte.

Power supply 102 is reactivated so that vial 141 is positively biased and vial 143 is negatively biased. This causes sample components that were injected clockwise to proceed toward detector 110 and vial 142. Incidently, sample components injected counterclockwise proceed toward vial 144. As sample components begin to separate, controller 116 monitors component peaks via detector 110. Controller 116 compares the time of a peak detection with the sample injection time or the previous peak detection time to determine a migration rate for the sample component represented by the peak. Detector 110 is located halfway between vials 141 and 142. Hence, if a group of peaks of interest takes time $t_1$ to travel from vial 141 to detector 110, it can be expected to require $2t_1$ to reach vial 142, and further even multiples of $t_1$ to reach successive vials. Also, one can extrapolate that the sample group will be midway between vials at odd multiples of $t_1$, and at detector 110 at $9t_1$, at $17t1$, and more generally at $t=(8n+1)t_1$, where n is a counting number.

At about time $2t_1$, the sample components are in bend 162. Due to the action of the voltage differential between vials 141 and 143, sample components travel along the separation path under the influence of field 1F1 so that sample is not lost though opening 172. At about $3t_1$, the sample components are halfway between vials 142 and 143. Incidentally, sample that was injected counter-clockwise has progressed upstream to about half way between vials 144 and 143 at this time.

At this time $3t_1$, distributor 104 switches so that vial 142 becomes the anode and vial 144 becomes the cathode. This switch does not change the field around the clockwise sample components which continue migration toward vial 143. However, the counterclockwise sample components reverse direction and progress downstream toward vial 144.

At time $4t_1$, the clockwise sample components arrive at bend 163, being drawn by separation field 1F2 past hole 173 without sample loss from capillary 106. At this time $4t_1$, counterclockwise sample components arrive at bend 164 and are pulled out of capillary 106 through opening 174 and into vial 144 by the voltage applied to electrode 134. Thus, the counterclockwise injected sample components are dumped so they do not interfere with the separation of the clockwise injected sample components. Even if some of the counterclockwise injected sample is not dumped at this stage, further dumping will occur at successive stages of the separation process, rendering any presence of counterclockwise-injected sample negligible.

At time $5t_1$, the clockwise sample components are about halfway between vials 143 and 144. Distributor 104 switches so that vial 143 becomes the anode and vial 141 becomes the cathode. Again, this switch does not change the electric field in the vicinity of the sample components which continue their clockwise migration. At time $6t_1$, clockwise sample components reach vial 144 and, at time $7t_1$, the distributor causes vial 144 to be the anode and vial 142 to be the cathode.

As sample components continue to separate, some lag and some lead the sample components of interest. Sample components leading by more than half a leg reach an anode before it is switched; these components are dumped as they reach the anode. Sample components lagging by more than half a leg are redirected clockwise on the next change of potentials. These components are then dumped at a cathode within one or more steps of distributor 104. It can thus be seen that, as separation is increased, dynamic range is lost. Thus, the present invention implements a "zoom" function, allowing an expanded view of a selected group of sample components.

At time $8t_1$, the sample components return to joint 161 to complete their first cycle. At time $9t_1$, they reach detector 110. Controller 116 monitors detector 110 to update distributor timing each cycle of a sample component around capillary 106. Each time the sample component passes detector 110, a new electropherogram is obtained; each successive electropherogram has a higher resolution than the preceding one. Once peaks of interest are satisfactorily resolved, separation can stop; thus, separation need not be continued beyond the time required to achieve the desired separation.

Figure 7:
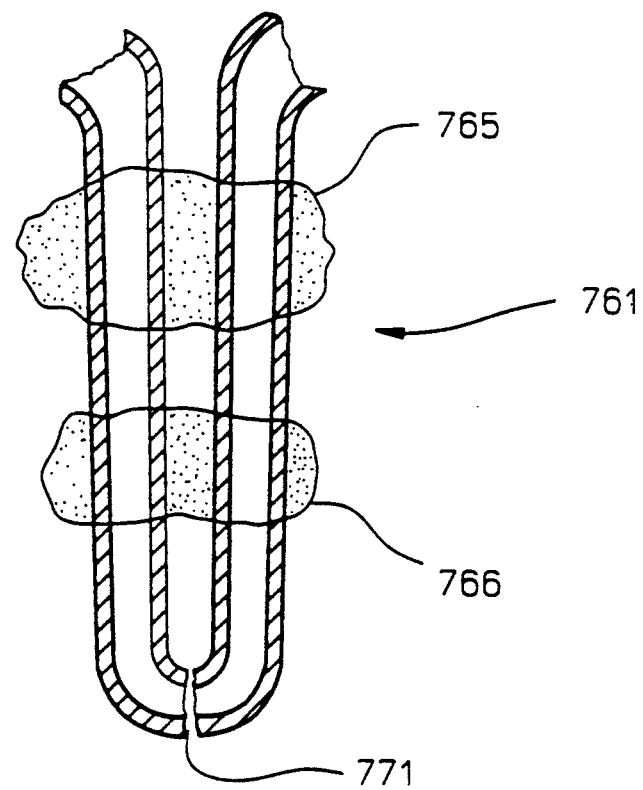
FIG. 7 is a schematic illustration of a joint employable in the three-point closed capillary electrophoresis system of FIG. 4.

Three-point closed capillary electrophoresis system 400, illustrated in FIG. 4, uses an alternative open bend 761, shown in FIG. 7, for use in a capillary electrophoresis system such as system 400. In this case, a triangular capillary 406 with bends is formed as above. A first epoxy 765 is applied to provide structural rigidity to bend 761, which is then scribed and fractured. The newly formed ends are then separated by 25 microns to define an opening 771. A second epoxy 766 is applied to maintain the separation. As an alternative to the earlier described method of forming a ring capillary configuration, the ends of an originally straight capillary can be joined, leaving an intermediate space to form a bend like that illustrated in FIG. 7.

The open hair-pin configurations for switching and gating samples and peaks of FIGS. 6 and 7 can be used to route a given peak into an auxiliary capillary. The auxiliary capillary can be used as a container for ease of handing and for minimizing evaporation.

Figure 8:
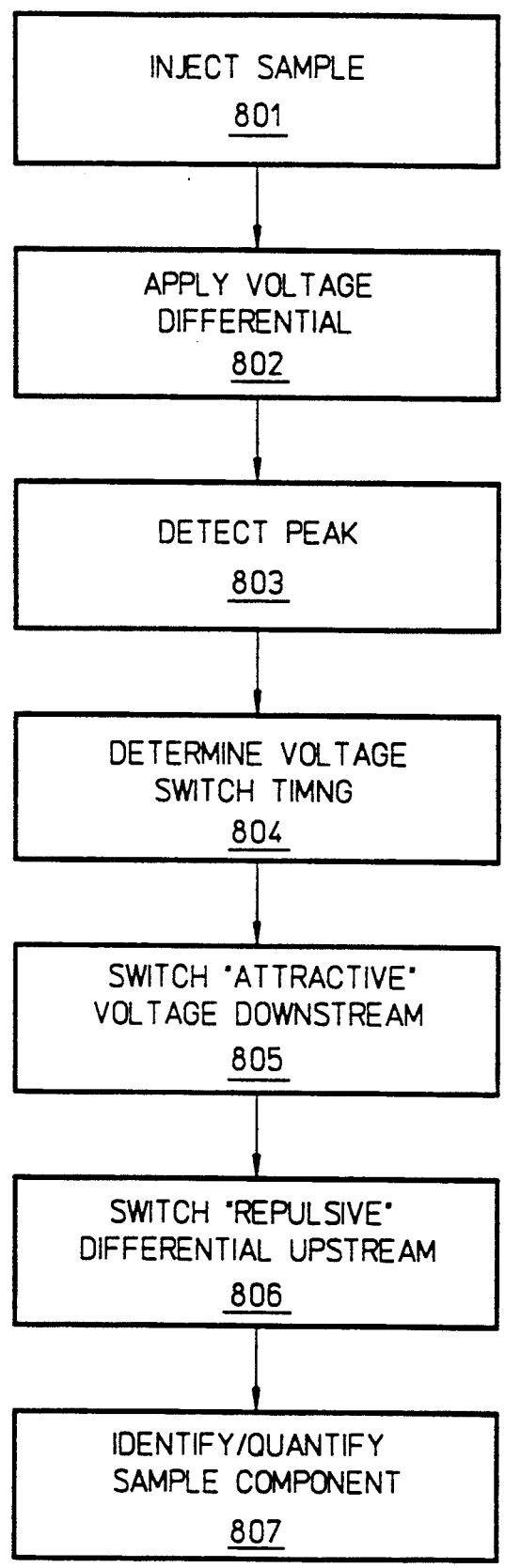
FIG. 8 is a flow chart of a separation method in accordance with the present invention.

The general separation method 800 of the present invention is flow-charted in FIG. 8. At step 801, a sample is injected into a capillary defining a separation path and a downstream direction. At step 802, a voltage differential is applied between an intermediate electrode point and an upstream electrode point (upstream of the intermediate electrode point); the sense of the voltage differential is selected so that a sample component of interest migrates downstream toward the intermediate electrode point. In other words, a "repulsive" voltage is applied to the upstream electrode point and an "attractive" voltage is applied to the intermediate electrode point. In practice, this voltage differential can also be used for sample injection at step 801.

At step 803, a sample component peak is detected. In practice, several peaks may be detected. Thus, step 803 can involve the selection of a particular peak for further high resolution analysis. The selection can be based on a predetermined selection of a component to be quantified. The peak corresponding to that component can be distinguished by a signature, such as its ultraviolet absorption spectrum. Alternatively, a group of overlapping peaks can be selected for eventual separation and identification.

At step 804, the timing of voltage switchings, i.e., the distributor timing is determined. For example distributor timing can be calculated from the migration rate of a sample component of interest. Migration rate determination can be accomplished by comparing the time of a peak detection with a reference time. The reference time can be the sample injection time or, more precisely, the time the injected sample is first subjected to a separation field. During subsequent detections, the reference time can be the time of the previous detection of the same peak. Thus, step 804 can be iterated to update timing. Instead of determining migration rate on line, the migration rate can be calculated off line from known characteristics of a sample of interest using the determined separation field strength. Of course, those skilled in the art can see that the distributor timing can also be calculated using the migration rate in principle without ever explicitly determining the migration rate.

At step 805, the "attractive" voltage is switched to an electrode point other than the intermediate electrode point. This other electrode point is selected so that the sample component continues to migrate downstream past the intermediate electrode point. The "repulsive" potential can remain at the original upstream electrode point, as in an "inch-worm" method. Alternatively, the repulsive potential can be moved synchronously, as occurs in a constant-field method. This step can be iterated until adequate separation has been achieved. The timing of the switching is calculated using the migration rate determined in step 804, as weighted by any changes in field strength over time, and the position of the last peak detection.

At step 806, the repulsive potential is applied to the intermediate electrode after the sample component has migrated past. In the inch-worm variant, only the repulsive potential is moved. In the constant-field variant, the attractive potential is moved to an electrode point further downstream. The timing for the voltage switch 806 is calculated in the same manner as the timing for step 805.

At step 807, once adequate separation has been achieved, sample identification and/or quantification can be performed. Preferably, the detector used in step 803 is used in step 807.

The present invention provides for several alternatives to the embodiments described above. Capillaries of different lengths and internal cross sections can be used. Capillaries can have interior cross sections that are circular, oval, rectangular, etc. The narrowest dimension of the cross sections are 100 microns or less.

A capillary with a 5 by 50 micron rectangular interior can be used to allow higher fields. The retention times are measured in minutes. The resulting peaks are so long, e.g., 4 times normal, that a larger bubble factor of perhaps 5x is in order, so that sensitivity is largely regained. Lower-frequency low-pass filtering further reduces noise. Sensitivity can be traded for speed and vice versa.

The capillaries can be in open or closed configurations. Openly configured capillaries can double back or spiral in a helix configuration so that they pass a single detector multiple times; thus, even in an open embodiment, a single detector can be used for both sample component tracking and for sample component identification and quantification. Other embodiments can use two or more detectors. A closed embodiment can use multiple detectors, for example, one per leg of a separation path to ensure tight tracking. Different types of detectors can be used depending on the sample components of interest. Different numbers of electrode points are provided for. Constant-voltage, inch-worm and ramp-type fields are provided for. These and other variations upon and modifications to the described embodiments are provided by the present invention, the scope of which is limited only by the following claims.

What is claimed is:

1. A capillary electrophoresis system comprising:
   capillary means for defining a separation path having a downstream direction, said separation path including at least three electrode points, said electrode points including an intermediate electrode point;
   power supply means for supplying a voltage differential;
   distributor means for selectively routing said voltage differential to pairs of said electrode points, said distributor means having at least two conditions including
      a first condition in which said voltage potential is applied between said intermediate electrode point and another of said electrode points so that a sample component migrates downstream toward said intermediate electrode point, and a second condition in which, before said sample component reaches said intermediate electrode point, said voltage differential can be applied between two of said electrode points other than said intermediate electrode point so that said sample component migrates downstream past said intermediate electrode point, said distributor means being electrically coupled to said power supply means and to said capillary means; and rate determination means for determining the migration rate of a sample component, said rate determination means including a controller coupled to said distributor so that said controller commands said distributor means to switch said voltage differential between pairs of said electrode points at times determined as a function of said migration rate so that said sample component migrates continuously in a downstream direction.

2. A capillary electrophoresis system as recited in claim 1 wherein said rate determination means includes a detector optically coupled to said capillary means so that said detector means outputs a detection signal in response to detection of said sample component, said detector means being coupled to said controller so that the detector output is received by said controller, said controller using said detector output to calculate said migration rate.

3. A capillary electrophoresis system comprising:

capillary means for defining a separation path including at least three electrode points including an intermediate electrode point;

power supply means for supplying a voltage differential; and distributor means for selectively routing said voltage differential to pairs of said electrode points, said distributor means having at least two conditions including a first condition in which said voltage potential is applied between said intermediate electrode point and another of said electrode points so that a sample component migrates downstream toward said intermediate electrode point, and a second condition in which, before said sample component reaches said intermediate electrode point, said voltage differential can be applied between two of said electrode points other than said intermediate electrode point so that said sample component migrates downstream past said intermediate electrode point, said distributor means being electrically coupled to said power supply means and to said capillary means, said separation path being closed to define a loop so that said sample component can cycle around said separation path multiple times.

4. A capillary electrophoresis system comprising:

capillary means for defining a closed separation loop having a downstream direction and an upstream direction;

four electrodes arranged in a closed series at four respective electrode points along said sample loop;

power supply means for supplying a voltage differential;

distributor means for applying said voltage differential to pairs of nonadjacent ones of said electrodes so that a first sample component migrate in said downstream direction and so that a second sample component migrates in said upstream direction; and controller means for driving said distributor means so that said first sample component migrates continuously in said downstream direction under a constant electric field strength.

5. A capillary electrophoresis system as recited in claim 4 further comprising detector means for detecting said first sample component, said detector means being optically coupled to said capillary means.

6. A capillary electrophoresis system as recited in claim 5 wherein said detector means is coupled to said controller means, said controller means including migration rate means for calculating the migration rate of said first sample component from the timing of sample component detections by said detector means, said controller means determining the rate at which said voltage differential is switched between said pairs of nonadjacent ones of said electrodes.

7. A method of separating sample components, said method comprising the steps of:

a) injecting a sample into a closed separation loop having a downstream direction and at least three electrode points, including an intermediate electrode point;

b) applying a voltage differential between said intermediate electrode point and another electrode point so that a first sample component migrates downstream toward said intermediate electrode point and so that a second sample component migrates upstream toward said intermediate electrode point; and c) before said sample component reaches said intermediate electrode point, switching the voltage differential to between two electrode points other than said intermediate electrode point so that said first sample component migrates downstream past said intermediate electrode point.

8. A method of separating sample components as recited in claim 7 further comprising a step d of, after step c, switching said voltage differential to between said intermediate electrode point and another of said electrode points so that said first sample component migrates downstream away from said intermediate electrode point.

9. A method of separating sample components as recited in claim 7 further comprising a step of determining the timing for the voltage switch of step c.

10. A method of separating sample components as recited in claim 7 further comprising a step of, before step c, detecting a peak associated with said first sample component.

11. A method of separating sample components, said method comprising the steps of:

a) injecting a sample into a separation path having a downstream direction and at least three electrode points, including an intermediate electrode point;

b) applying a voltage differential between said intermediate electrode point and another electrode point so that a sample component migrates downstream toward said intermediate electrode point;

c) detecting a peak associated with said sample component;

d) before said sample component reaches said intermediate electrode point, switching the voltage differential to between two electrode points other than said intermediate electrode point so that said sample component migrates downstream past said intermediate electrode point; and e) determining the timing of the voltage switching of step d as a function of the time of said detecting step and a reference time.

12. A method of separating sample components comprising the steps of:
   a) injecting a sample into a closed separation loop having a downstream direction, a first electrode point, a second electrode point, a third electrode point, and a fourth electrode point, said first, second, third and fourth electrode points being downstream adjacent respectively to said fourth, first, second and third electrode points, said first electrode point and said third electrode point opposing each other, said second electrode point and said fourth electrode point opposing each;
   b) applying a voltage differential between said first electrode point and said third electrode point so that a first sample component of said sample migrates downstream past said second electrode point and a second sample component of said sample migrates upstream toward said fourth electrode point;
   c) as said first sample component approaches an electrode point from the immediately adjacent upstream electrode point, switching the voltage differential from the pair including that electrode point and the opposing electrode point to the pair including the two electrode points adjacent to the approached electrode point so that said first sample component can migrate downstream past said approached electrode point; and
   d) iterating step c for successive downstream electrode points;
   whereby, sample components are progressively separated as they cycle said closed separation loop.

13. A method of separating sample components as recited in claim 12 further comprising detecting when said first sample component passes a detection point along said separation loop, and determining the timing of the switching of iterated step d as a function of this migration rate.

* * * * *